US009250620B2

(12) United States Patent
Kotlus

(10) Patent No.: US 9,250,620 B2
(45) Date of Patent: Feb. 2, 2016

(54) 3D DESIGN AND FABRICATION SYSTEM FOR IMPLANTS

(71) Applicant: Brett Kotlus, Long Island, NY (US)

(72) Inventor: Brett Kotlus, Long Island, NY (US)

(*) Notice: Subject to any disclaimer, the term of this patent is extended or adjusted under 35 U.S.C. 154(b) by 0 days.

(21) Appl. No.: 14/669,576

(22) Filed: Mar. 26, 2015

(65) Prior Publication Data

US 2015/0198943 A1 Jul. 16, 2015

Related U.S. Application Data

(63) Continuation-in-part of application No. 13/789,814, filed on Mar. 8, 2013, now Pat. No. 9,056,017.

(60) Provisional application No. 61/608,198, filed on Mar. 8, 2012.

(51) Int. Cl.
| | |
|---|---|
| *A61F 2/44* | (2006.01) |
| *G05B 19/4097* | (2006.01) |
| *A61F 2/00* | (2006.01) |
| *A61F 2/30* | (2006.01) |
| *G06F 17/50* | (2006.01) |
| *G06T 19/20* | (2011.01) |
| *A61B 19/00* | (2006.01) |
| *B29C 67/00* | (2006.01) |
| *G06F 19/00* | (2011.01) |

(52) U.S. Cl.
CPC .......... *G05B 19/4097* (2013.01); *A61F 2/0059* (2013.01); *A61F 2/30942* (2013.01); *A61F 2/442* (2013.01); *G06F 17/50* (2013.01); *G06T 19/20* (2013.01); *A61B 2019/502* (2013.01); *A61B 2019/507* (2013.01); *A61B 2019/508* (2013.01); *A61F 2/44* (2013.01); *A61F 2002/30948* (2013.01); *A61F 2002/444* (2013.01); *B29C 67/0059* (2013.01); *G06F 19/3437* (2013.01); *G06T 2200/08* (2013.01); *G06T 2219/2021* (2013.01); *Y10T 29/49* (2015.01)

(58) Field of Classification Search
CPC .............................. A61F 2/442; G06T 19/20
See application file for complete search history.

(56) References Cited

U.S. PATENT DOCUMENTS

| | | | | |
|---|---|---|---|---|
| 2005/0148843 | A1* | 7/2005 | Roose | A61B 17/17 600/407 |
| 2007/0233272 | A1* | 10/2007 | Boyce | A61B 17/0401 623/23.63 |

* cited by examiner

*Primary Examiner* — Andrew Yang
(74) *Attorney, Agent, or Firm* — Kohn & Associates, PLLC

(57) ABSTRACT

A method of designing, presenting, generating, and fabricating custom implants by obtaining a 3D image of a site to receive an implant, simulating volumetric changes of the site, generating a virtual 3D implant that effects the volumetric changes of the site, and fabricating a real 3D implant that includes the volumetric changes. A method of designing, presenting, generating, and implanting custom implants by obtaining a three-dimensional (3D) image of a site to receive an implant, simulating volumetric changes of the site, generating a virtual 3D implant that effects volumetric changes of the site, and injecting or infusing a gel or semi-solid implant into a patient to effect the volumetric changes. A method of implanting a custom implant in a patient. A method of correcting disfigurement in a patient. A method of replacing a disc in a patient's back. An implant fabricated by this method.

21 Claims, 6 Drawing Sheets

3D DESIGN AND FABRICATION SYSTEM FOR IMPLANTS

BACKGROUND OF THE INVENTION

1. Technical Field

The present invention relates to methods of fabricating aesthetic and reconstructive surgical implants. More specifically, the present invention relates to methods of generating custom implants.

2. Background Art

After serious injury or disease, restoration of normal function, symmetry, and appearance can require surgery involving implanting materials to reshape the affected area of the body. Implants are also used to augment the shape and volume of normal anatomic regions of the body for aesthetic purposes. For the most part, commonly used implants are generic, prefabricated shapes and sizes that must be fit to each individual as best as they can. In other words, the majority of implants available are not specifically tailored to a patient and do not take normal asymmetry or other unique qualities into account.

There are several methods of generating implants that are currently used. U.S. Pat. No. 7,747,305 to Dean, et al. is one particular method of generating an implant based on a 3D CT scan. The '305 patent discloses a computer aided design method for producing an implant for a patient prior to operation comprising the steps of: generating data with a non-invasive 3D (3-dimensional) scan of the patient's defect site that digitally represents the area that will receive the implant; designing and validating an implant on a computer based on digital data generated from a volume image of the patient; and fabricating the implant based solely on the implant design data generated on computer.

U.S. Patent Application Publication No. 2006/0212158 to Miller generally discloses a device and method of manufacturing and implanting a custom subtalar arthroereisis implant having side surfaces, which are mirrored in topography with the sinus tarsi of a patient. The implant is formed using images of the patient standing in a weight bearing position with their sinus tarsi and the surrounding bone structure in an anatomically correct alignment. These 3D images can be obtained by a CAT scanner or an MRI device. Formation of the implant can be accomplished by three dimensional printers or computer driven mills. Once implanted, the implant urges and maintains the anatomically correct alignment thereby minimizing any patient tendency for abnormal motion between said patent's talus and calcaneus.

U.S. Patent Application Publication No. 2006/0212158 to Feldman generally discloses a device and method of manufacturing and implanting a custom subtalar arthroereisis implant having side surfaces, which are mirrored in topography with the sinus tarsi of a patient. The implant is formed using images of the patient standing in a weight bearing position with their sinus tarsi and the surrounding bone structure in an anatomically correct alignment. These 3D images can be obtained by a CAT scanner or MRI device. Once the image is sent to the computer, 3D modeling software (with physics modeling) can be used (Mimics Software Suite Materialise) to modify the implant. The implant can be formed by a three-dimensional printer or CNC machine. Once implanted, the implant urges and maintains the anatomically correct alignment thereby minimizing any patient tendency for abnormal motion between said patent's talus and calcaneus.

Custom implants can be developed from MRI or CT scans as in the methods above; however, they have several drawbacks. Patients receive radiation from CT scans and both MRI and CT scans are quite expensive to perform. The implants must generally be fabricated off-site at a laboratory or manufacturing location with injection molding and require a turn-around time of several days to several weeks. They can be unshaped materials (blocks) that are carved by hand, which is tedious and inaccurate. They do not allow for visualization of a simulated surgical outcome. Also, they do not allow for customization with virtual 3D external photographs. They do not visually predict the soft tissue modifications that will occur after implantation.

Therefore, there remains a need for a method of complete customization of an implant for a patient with on-site implant creation within hours that is lower cost than present methods.

SUMMARY OF THE INVENTION

The present invention provides for a method of designing, presenting, generating, and fabricating custom implants by obtaining a 3D image of a site to receive an implant, simulating volumetric changes of the site, generating a virtual 3D implant that effects the volumetric changes of the site, and fabricating a real 3D implant that includes the volumetric changes.

The present invention provides for a method of designing, presenting, generating, and implanting custom implants by obtaining a three-dimensional (3D) image of a site to receive an implant, simulating volumetric changes of the site, generating a virtual 3D implant that effects the volumetric changes of the site, and injecting or infusing a gel or semi-solid implant into a patient to effect the volumetric changes.

The present invention provides for a method of implanting a custom implant in a patient, by obtaining a 3D image of a site to receive an implant, simulating volumetric changes of the site, generating a virtual 3D implant that effects the volumetric changes of the site, fabricating a real 3D implant that includes the volumetric changes, and implanting the implant in the patient.

The present invention also provides for a method of correcting disfigurement in a patient, by obtaining a 3D image of a site to receive an implant, simulating volumetric changes of the site, generating a virtual 3D implant that effects the volumetric changes of the site, fabricating a real 3D implant that includes the volumetric changes, and implanting the implant in the patient and correcting the disfigurement.

The present invention further provides for a method of replacing a disc in a patient's back, by obtaining a 3D image of an intervertebral space in the back, simulating volumetric changes of the intervertebral space, generating a virtual 3D disc that effects the volumetric changes of the site, fabricating a real 3D disc that includes the volumetric changes, and implanting the disc in the patient's back.

The present invention also provides for an implant fabricated by this method.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

The present invention is generally directed to a method of designing, presenting, generating, and fabricating custom implants, preferably for use in humans, based on 3D imaging. The customization is based on individual anatomic findings, taking into account pre-existing asymmetries, unique structures, and desired modifications, thus obviating the need for generic implants. The method allows for visualization of a virtual implant's external appearance (i.e. how the implant will appear from the outside when implanted under the body tissues) before implantation takes place. The method is also dictated by the desired appearance, fit, and function of the virtual implant.

Figure 7:
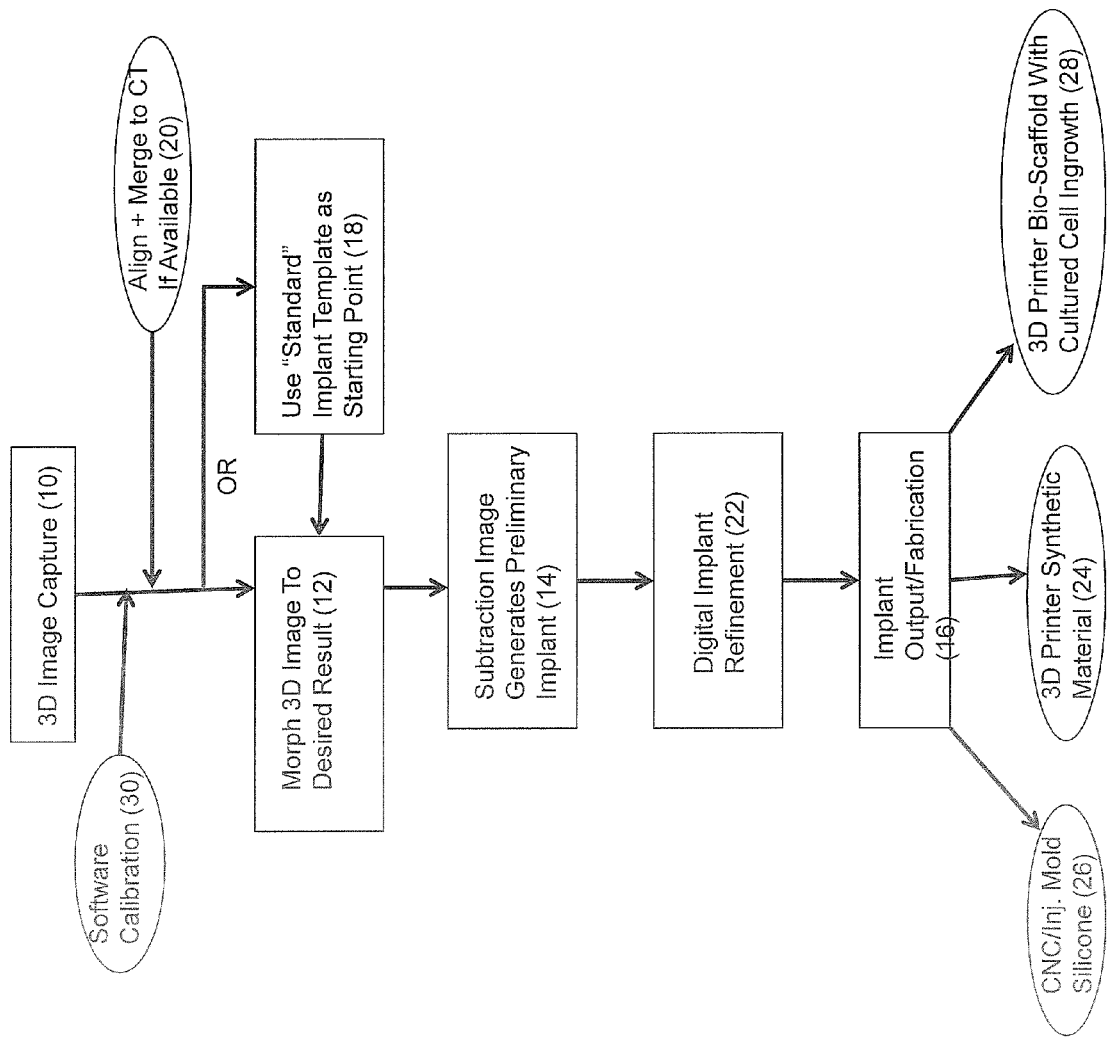
FIG. 7 is a flow chart of the method of the present invention.

More specifically, the method includes obtaining an external 3D image of a site or area of the body to receive an implant 10, simulating volumetric changes of the site 12, generating a virtual 3D implant 14 that effects the volumetric changes of the site, and fabricating a real 3D implant 16 that includes the volumetric changes. These steps are generally shown in FIG. 7. The present invention also provides for an implant fabricated by this method.

Figure 1:
FIG. 1 is a photograph of generating an external 3D image in the method of the present invention.

There are several ways that an external 3D image can be obtained. As shown in FIG. 1, multiple still digital photographs are taken from various angles of a site or area of the body on the patient that is to receive the implant. Several cameras can be used to take the photographs. For example, six digital cameras (such as by Canfield Scientific, Inc.) can be used to capture images of the site. A 3D camera can be used but any other camera can also be used along with software that can integrate images from different angles to obtain a 3D image. Any other suitable combination of cameras can be used to obtain a 3D image. For example, a smartphone, tablet, a video camera, or any other high-resolution image capture device can be used to obtain still images that can be used to generate a 3D image. Merged video can be used. Alternatively, a 3D scanner can be used to obtain the 3D image by scanning the site. The 3D scanner moves around the patient to capture the 3D surface information in order to obtain the 3D image. The scanner can be a laser, infrared, or light type of scanner. Whether cameras or scanners are used, the 3D image can be stored on the device itself with computer readable media and/or sent to a computer via wireless or wired signals and stored with computer readable media directly on the computer.

Figures 2A, 2B:
FIGS. 2A and 2B are photographs of simulating volumetric changes of the implant site.

Next, volumetric changes of the site or area of the body are simulated on the external photo (as shown in FIGS. 2A and 2B with the chin area) and can be displayed to the patient. Preferably, this is done by morphing tools on a computer. For example, the morphing tool can be Canfield Mirror (Canfield Scientific, Inc.), or any other suitable morphing software. These morphing tools can be calibrated as necessary by one skilled in the art (shown at 30 in FIG. 7). The desired shape of the implant can be simulated with the morphing tools alone. In other words, the implant can be generated by morphing an area of the body of patient with the morphing tools in the computer software, and based on the adjustments to the body, the computer software can determine and calculate what the implant needs to look like (i.e. size and shape). A suitable standard implant to use can be determined and selected by the computer software, and then the standard implant can be adjusted to customize the fit by the fabrication methods described below. The subtraction of before and after morphing results in a difference model, which is the basis for the implant shape and size. Alternatively, based on the calculations, a completely custom implant can be created instead of starting with a standard implant. The software uses physics modeling (using predictive modeling and simulated biophysical characteristics and behavior) to simulate external appearances and predicts the influence of the implant on the surrounding structures and tissues. Different implant materials can be simulated within the design system based on known traits and qualities (softness, pliability, etc) to determine the response of the surrounding tissue and the end appearance.

Alternatively, the morphing tools can include the use of pre-determined standard implant shapes that are pre-loaded in the software that can be modified after simulated implantation (shown at 18 in FIG. 7). In other words, the starting point for morphing the patient's body can be a standard implant shape. From here, the 3D image can be morphed to customize the standard implant shape and achieve the desired result in the patient's body. For example, further changes to the standard implant can modify the anterior surface of the proposed implant, which the shape of the posterior surface remains as the "standard" curvature. In other words, the software uses physics modeling to simulate external appearance and predicts the influence of the implant on the surrounding structures and tissues. One advantage of using a standard predetermined shape is that bone imaging may not always be required and the method can be simplified.

Regardless of whether the patient's body is morphed first from the software, or whether a standard implant is chosen and subsequently adjusted, the present invention is advantageous over methods in the prior art because the resulting look from the morphed 3D image can be displayed to the patient and they can decide if they do not find the implant acceptable or to their liking, and adjustments can be made in real time until they are satisfied and approve of the morphed 3D image.

Another alternative is to take and use a CT or MRI image for an externally captured image of the patient to determine the posterior surface of the implant and the 3D image obtained in the above step to determine the anterior surface of the implant. The 3D photographic image can also be aligned with a 3D CT image (shown at 20 in FIG. 7) so that both images can be used at the same time to determine how the implant interacts with bone and how the implant interacts with soft tissue. Internal images (i.e. skeletal bone images) can also be captured with CT, MRI, cone beam CT scan (CBCT, a 3D fast scan x-ray), or ultrasound and can further be used to aid in obtaining an image of the site. Any of these additional images can be merged and aligned with each other (i.e. external images merged and aligned with internal images, etc.) Also, the implant shape can be adjusted based on the vital structures identified in the body scan (CT, MRI, CBCT, ultrasound) including nerves, blood vessels, muscle, bone, organs, and connective tissue.

The morphing tools can also include complete customization by use of bulge and warp tools to modify the 3D external image and an implant can be created based on the determined difference volume between the original image and the morphed image. Further modifications can be made to the isolated difference model.

Figure 3:
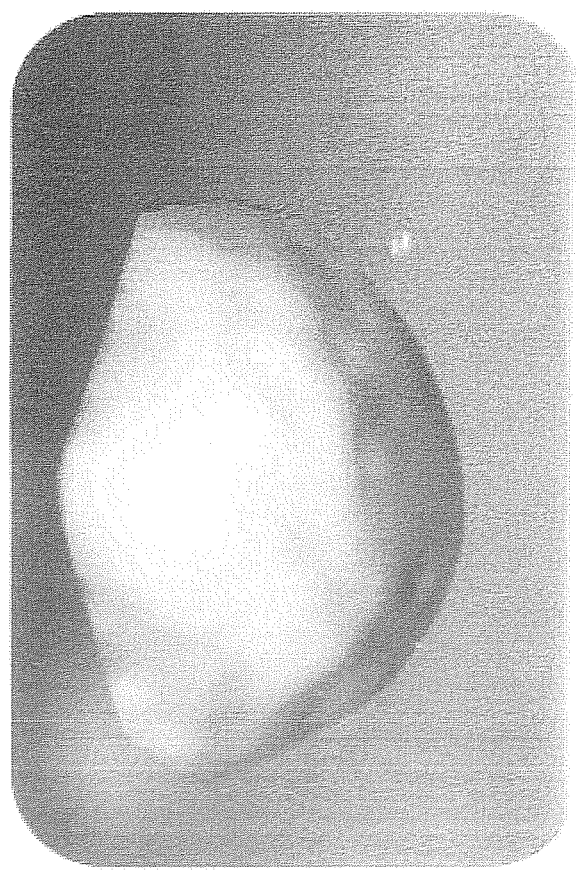
FIG. 3 is an image of a virtual 3D implant.
Figure 4:
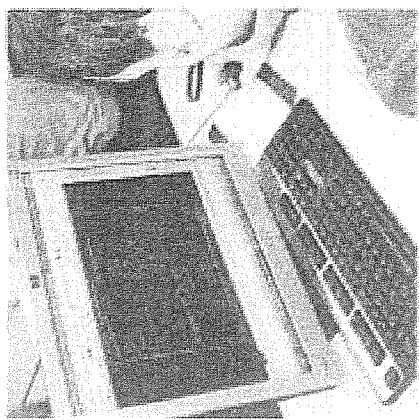
FIG. 4 is a photograph showing making adjustments with a CAD file.

Next, a virtual 3D implant is generated by a computer software tool that achieves the desired volume and contour change, as shown in FIG. 3. This software tool can be the same as that used in the previous step, or it can be any other suitable computer software. The 3D implant is viewed in the software and adjustments and refinements can be made to the dimensions and checked against the patient's 3D images to achieve the final design, as shown in FIG. 4 and shown at 22 in FIG. 7. Any suitable desired changes or refinement can be made at this point, such as, but not limited to, adjustments to shape, dimension, edges, size, smoothness, position, orientation, symmetry, and projection. Virtual tools can be used to dictate implant shape for post-traumatic reconstruction and display how the reconstructed body region looks externally with the implant in place in order to add more specific detail about reconstruction. Virtual tools can be used to achieve symmetry between bilateral physical structures. This allows for mirroring of normal structures when damage or asymmetry is present on a paired body structure.

After the changes and refinements, the implant is "re-simulated" in the original presurgical imaging performed above and shown to the patient. In other words, the refined virtual implant can be re-situated in the original, untouched 3D image to test appropriateness, feasibility, and desirability of the refinements. Further adjustments with the morphing tools as above can be performed and the adjustments and refinements can be performed repeatedly until the patient is satisfied and the ideal implant is achieved. The virtual 3D implant (and any other required information) is saved on computer readable media (preferably in the form of a CAD file). The file is then sent to a fabrication machine via wireless or wired communication.

The data from the method of implant creation can also be used to aid in surgical implantation and prepare for surgical implantation. The final implant and 3D images can be used to create a virtual simulation of a surgical procedure to place the implant in the patient, including presentation and selection of approach options which can be shown to the patient during consultation or with other medical personnel. The implant and 3D images can also be used to allow a surgeon or medical student to practice virtual surgery with the images and the implant. The images can also be used intra-operatively for reference, problem solving, structure identification, and overall surgical aid.

At this point, optionally, the implant can be fabricated with plastic, acrylic, or other test material for confirmation before the final manufacturing. The surrounding tissue/structures/skeleton of the patient can also be fabricated in synthetic material for use in pre-surgical and/or intraoperative planning. A CNC machine can be used or a 3D printer for these steps.

Figure 5B:
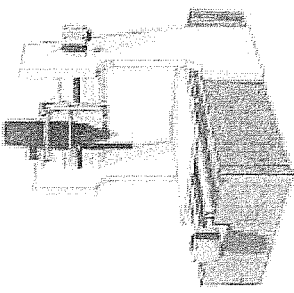
FIG. 5A is an image of a 3D printer and FIG. 5B is an image of a CNC machine.
Figure 5A:
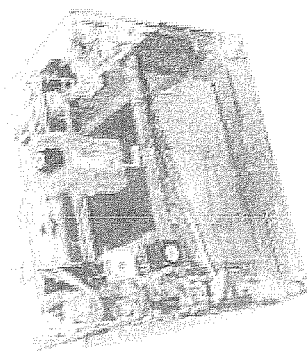
Figure 6:
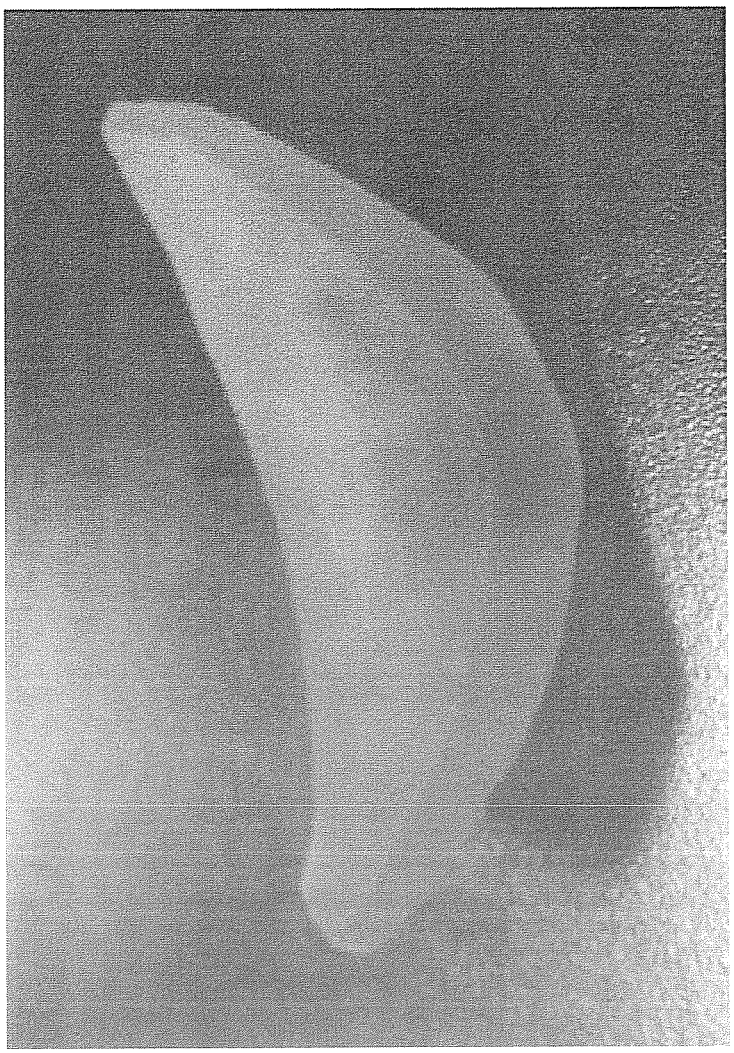
FIG. 6 is a photograph of an implant prepared by the method of the present invention.

The real 3D implant is fabricated from the virtual 3D implant with a biocompatible material using the fabrication machine. The method of the present invention generally uses the computer software in order to control robotics to produce an implant. The fabrication machine can be a 3D printer (FIG. 5A, 24 in FIG. 7), a CNC machine (FIG. 5B, 26 in FIG. 7), or an injection molding machine. A 3D printer uses an additive method of fabrication in order to generate the 3D implant. A CNC machine uses a subtractive method in order to carve or mill the material directly to generate the 3D implant. Also, the negative image can be milled to create a mold that is injected with material that then becomes the final implant. The use of a 3D printer/CNC machine allows for the implant to be fabricated directly in a physician's office or other location. A finished and fabricated implant is shown in FIG. 6.

The implant can generally be made from solid, semi-solid, gel, or scaffolding materials and can be synthetic or biomaterials. The materials that can be used can be, but are not limited to, silicone, hard silicone, polymethylmethacrylate (PMMA), porous polyethylene, polytetrafluoroethylene (PTFE), PEEK (polyetheretherketone), PEKK (polyetherketoneketone), expanded polytetrafluoroethylene (e-PTFE), acellular dermis, autologous dermal-fat, bone grafts, other synthetic bone analogues, titanium, gold, polygalactin, synthetic bone, hydrogel, hyaluronic acid, or hydroxylapatite. The materials can also include those that allow for cultured tissue growth or cell ingrowth, such as a collagen matrix or synthetic live material, bioscaffolding (such as with living cells), or printed live tissue (shown at 28 in FIG. 7). The implant can be populated with cells after the initial fabrication.

After fabrication, the implant can be sterilized and/or prepared for implantation in the patient.

When the material is a gel or semi-solid, the implant can be injected or infused into the patient's body instead of being fabricated based on the virtual tools. Therefore, the present invention provides for a method of designing, presenting, generating, and implanting custom implants by obtaining a three-dimensional (3D) image of a site to receive an implant, simulating volumetric changes of the site, generating a virtual 3D implant that effects the volumetric changes of the site, and injecting or infusing a gel or semi-solid implant into a patient to effect the volumetric changes. By generating the virtual 3D implant, it can be determined how much gel or semi-solid is needed and where it should be injected or infused in order to create the desired look. More specifically, this method can be used with hydrogels and collagen matrix materials, hyaluronic acid and other hyaluron derivatives, polymethymethacrylate (PMMA) suspensions, calcium hydroxyapatite suspensions, poly-l-lactic acid, collagen, gelatin, autologous dermal proteins, autologous fat, autologous fibroblasts, plant-derived injectable fillers, silicone, acrylamide, or polyalkylimide.

The method of the present invention can be used for any part of the body that requires an implant, such as, but not limited to, the face (chin, cheek, nose, temple, brow, tear trough, orbital rim, orbit, mandible, skull, etc.), the body (the knees, the elbows, chest, breast, buttocks, calf, etc.), or skeletal (joint, spine or back, etc.). The FIGURES in particular show an example of a chin implant.

The method of the present invention can be used in many different applications for which implants are desired or needed, both for aesthetic reasons as well as functional and therapeutic reasons. The method can be used for disfigurement, whether one that the patient was born with or is caused by accident or disease. The method can be used for improvement of physical features.

Most generally, the present invention provides for a method of implanting a custom implant in a patient, by obtaining a 3D image of a site to receive an implant, simulating volumetric changes of the site, generating a virtual 3D implant that effects the volumetric changes of the site, fabricating a real 3D implant that includes the volumetric changes, and implanting the implant in the patient.

The present invention also provides for a method of correcting disfigurement in a patient, by obtaining a 3D image of a site to receive an implant, simulating volumetric changes of the site, generating a virtual 3D implant that effects the volumetric changes of the site, fabricating a real 3D implant that includes the volumetric changes, and implanting the implant in the patient and correcting the disfigurement.

Another example of an implant that can be generated from this method is a disc replacement for the back. By using this method, a standard disc implant can be adjusted to fit the patient perfectly in customized fit in order to expand the intervertebral space. Alternatively, a completely custom implant can also be fabricated according to the steps described above.

Therefore, the present invention provides for a method of replacing a disc in a patient's back, by obtaining a 3D image of an intervertebral space in the back, simulating volumetric changes of the intervertebral space, generating a virtual 3D disc that effects the volumetric changes of the site, and fabricating a real 3D disc that includes the volumetric changes, and implanting the disc in the patient's back.

There are several advantages to the method of the present invention. This method improves on previous approaches by creating complete bespoke customization of implants with on-site implant creation within hours, instead of days or weeks. The method allows the physician to view the effects of the implant on soft tissue and how the patient will actually look after the implantation. It predicts how skin, muscle, fat, and soft tissue will appear with the underlying volume modification. It also gives the patient a simulated idea of their external appearance. Furthermore, the physician can morph the external appearance and generate an appropriate implant instead of guessing how the patient will look by modifying the skeletal structure. This method does not necessarily require radiation to the patient (unless combined with a CT scan), is much less expensive, and much quicker than previous methods.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of designing, presenting, generating, and fabricating custom implants, including the steps of:
   obtaining a three-dimensional (3D) image of a site to receive an implant;
   simulating volumetric changes of the site;
   generating a virtual 3D implant that effects the volumetric changes of the site; and
   fabricating a real 3D implant that includes the volumetric changes.

2. The method of claim 1, wherein said simulating step is further defined as using morphing tools to simulate different implant materials based on known traits and qualities, determining a response of surrounding tissue, and determining an end appearance.

3. The method of claim 1, wherein said simulating step is further defined as using an internally captured image and adjusting the shape of the implant based on a structure chosen from the group consisting of nerves, blood vessels, muscle, bone, organs, connective tissue, and combinations thereof.

4. The method of claim 3, wherein the internally captured image is chosen from the group consisting of a CT scan, MRI, cone beam CT scan (CBCT), and ultrasound.

5. The method of claim 1, wherein said generating step further includes the step of refining the 3D implant by adjusting a feature chosen from the group consisting of shape, dimension, edges, size, smoothness, position, orientation, symmetry, projection, and combinations thereof, and checking against the 3D image of the patient.

6. The method of claim 1, wherein said generating step further includes the step of using virtual tools to dictate the implant shape for post-traumatic reconstruction and display how the reconstructed body region looks externally with the implant in place.

7. The method of claim 1, wherein said generating step further includes the step of achieving symmetry between bilateral physical structures and mirroring normal structures when damage or asymmetry is present on a paired body structure.

8. The method of claim 1, further including after said generating step, the step of using data generated in the method to aid and prepare for surgical implantation.

9. The method of claim 8, wherein said using step is further defined as using the final implant and 3D images to create a virtual simulation of a surgical procedure to place the implant in the patient.

10. The method of claim 9, wherein the virtual simulation includes presentation and selection of approach options.

11. The method of claim 8, wherein said using step is further defined as using the implant and 3D images to allow a surgeon or medical student to practice virtual surgery with the images and the implant.

12. The method of claim 8, wherein said using step is further defined as using the 3D images intra-operatively for a reason chosen from the group consisting of reference, problem solving, structure identification, overall surgical aid, and combinations thereof.

13. The method of claim 1, wherein the implant is made of a material chosen from the group consisting of silicone, polymethylmethacrylate (PMMA), porous polyethylene, polytetrafluoroethylene (PTFE), PEEK (polyetheretherketone), PEKK (polyetherketoneketone), expanded polytetrafluoroethylene (e-PTFE), acellular dermis, autologous dermal-fat, bone grafts, other synthetic bone analogues, titanium, gold, polygalactin, synthetic bone, hydrogel, hyaluronic acid, hydroxylapatite, collagen matrix, synthetic live material, bioscaffolding, and printed live tissue.

14. The method of claim 1, wherein the implant is made of a material that allows for cell growth and wherein the implant is populated with cells after said fabricating step.

15. A method of designing, presenting, generating, and implanting custom implants, including the steps of:
   obtaining a three-dimensional (3D) image of a site to receive an implant;
   simulating volumetric changes of the site;
   generating a virtual 3D implant that effects the volumetric changes of the site; and
   injecting or infusing a gel or semi-solid implant into a patient to effect the volumetric changes.

16. The method of claim 15, wherein the gel or semi-solid is chosen from the group consisting of hydrogels, collagen matrix, hyaluronic acid and other hyaluron derivatives, polymethymethacrylate (PMMA) suspensions, calcium hydroxyapatite suspensions, poly-l-lactic acid, collagen, gelatin, autologous dermal proteins, autologous fat, autologous fibroblasts, plant-derived injectable fillers, silicone, acrylamide, and polyalkylimide.

17. A method of implanting a custom implant in a patient, including the steps of:
   obtaining a three-dimensional (3D) image of a site to receive an implant;
   simulating volumetric changes of the site;

generating a virtual 3D implant that effects the volumetric changes of the site;

fabricating a real 3D implant that includes the volumetric changes; and implanting the implant in the patient.

18. A method of correcting disfigurement in a patient, including the steps of:

obtaining a three-dimensional (3D) image of a site to receive an implant;

simulating volumetric changes of the site;

generating a virtual 3D implant that effects the volumetric changes of the site;

fabricating a real 3D implant that includes the volumetric changes; and implanting the implant in the patient and correcting the disfigurement.

19. The method of claim 18, wherein the disfigurement is to the face.

20. A method of replacing a disc in a patient's back, including the steps of:

obtaining a three-dimensional (3D) image of an intervertebral space in the back;

simulating volumetric changes of the intervertebral space;

generating a virtual 3D disc that effects the volumetric changes of the site;

fabricating a real 3D disc that includes the volumetric changes; and implanting the disc in the patient's back.

21. An implant fabricated by the method of claim 1.

* * * * *